(12) United States Patent
Tan et al.

(10) Patent No.: US 12,303,268 B2
(45) Date of Patent: May 20, 2025

(54) SYSTEMS AND METHODS FOR DETECTING MENTAL FATIGUE BY A USER OF AN IHS (INFORMATION HANDLING SYSTEM)

(71) Applicant: Dell Products, L.P., Round Rock, TX (US)

(72) Inventors: Loo Shing Tan, Singapore (SG); Seng Khoon Teh, Singapore (SG); Ruizhi Joyce Lu, Singapore (SG)

(73) Assignee: Dell Products, L.P., Round Rock, TX (US)

( * ) Notice: Subject to any disclaimer, the term of this patent is extended or adjusted under 35 U.S.C. 154(b) by 562 days.

(21) Appl. No.: 17/651,735

(22) Filed: Feb. 18, 2022

(65) Prior Publication Data

US 2023/0263440 A1    Aug. 24, 2023

(51) Int. Cl.
| | |
|---|---|
| *A61B 5/16* | (2006.01) |
| *A61B 5/00* | (2006.01) |
| *A61B 5/0205* | (2006.01) |
| *A61B 5/024* | (2006.01) |
| *A61B 5/08* | (2006.01) |
| *G16H 40/63* | (2018.01) |
| *G16H 50/30* | (2018.01) |

(52) U.S. Cl.
CPC ............ *A61B 5/165* (2013.01); *A61B 5/0205* (2013.01); *A61B 5/163* (2017.08); *A61B 5/486* (2013.01); *A61B 5/681* (2013.01); *A61B 5/6897* (2013.01); *A61B 5/7267* (2013.01); *A61B 5/7282* (2013.01); *G16H 40/63* (2018.01); *G16H 50/30* (2018.01); *A61B 5/02438* (2013.01); *A61B 5/0816* (2013.01); *A61B 2503/24* (2013.01)

(58) Field of Classification Search
CPC ....... A61B 5/165; A61B 5/0205; A61B 5/163; A61B 5/486; A61B 5/681; A61B 5/6897; A61B 5/7267; A61B 5/7282; A61B 5/02438; A61B 5/0816; A61B 2503/24; A61B 2503/20; G16H 40/63; G16H 50/30; G16H 10/20; G16H 50/70; G16H 50/20
See application file for complete search history.

(56) References Cited

U.S. PATENT DOCUMENTS

2022/0187912 A1* 6/2022 Alcaide ................... G06F 21/32

FOREIGN PATENT DOCUMENTS

| CN | 114783552 | * | 7/2022 | ............. G06F 30/27 |
| CN | 118845016 | * | 10/2024 | |
| NL | 2036641 | * | 3/2024 | ............. A61B 5/168 |

* cited by examiner

*Primary Examiner* — Mark W. Bockelman
(74) *Attorney, Agent, or Firm* — Fogarty LLP

(57) ABSTRACT

Systems and methods are provided for detecting mental fatigue by a user of an Information Handling System (IHS). Upon the user initiating operation of the IHS, activity by the user and physiological parameters of the user are monitored using capabilities of the IHS and, in some cases by wearable devices. Estimates of the user's mental fatigue during the session are generated based on the monitoring. Embodiments identify when the user takes a break from operating the IHS and also identify when the user resumes use of the IHS. Upon the user resuming the session, the user is prompted for their level of mental fatigue prior to taking the break, thus providing a reliable source of feedback data that is utilized in updating and improving machine learning models that are used to generate the estimates of the user's mental fatigue based on observed physiological parameters and activity by the user.

20 Claims, 3 Drawing Sheets

SYSTEMS AND METHODS FOR DETECTING MENTAL FATIGUE BY A USER OF AN IHS (INFORMATION HANDLING SYSTEM)

FIELD

This disclosure relates generally to Information Handling Systems (IHSs), and more specifically, to managing use of IHSs.

BACKGROUND

As the value and use of information continues to increase, individuals and businesses seek additional ways to process and store information. One option is an Information Handling System (IHS). An IHS generally processes, compiles, stores, and/or communicates information or data for business, personal, or other purposes. Because technology and information handling needs and requirements may vary between different applications, IHSs may also vary regarding what information is handled, how the information is handled, how much information is processed, stored, or communicated, and how quickly and efficiently the information may be processed, stored, or communicated. The variations in IHSs allow for IHSs to be general or configured for a specific user or specific use such as financial transaction processing, airline reservations, enterprise data storage, global communications, etc. In addition, IHSs may include a variety of hardware and software components that may be configured to process, store, and communicate information and may include one or more computer systems, data storage systems, and networking systems.

IHSs that are utilized for personal use, such personal computers, laptops, tablets, smartphones, etc., are increasingly likely to be regularly utilized for long intervals of time. Uninterrupted use of IHSs without breaks has been demonstrated to be potentially harmful, both physically and psychologically, to the user. In some instances, long intervals of uninterrupted use of an IHS may be intentional, such as in gameplay. However, in many instances, long intervals of uninterrupted use of an IHS may be through lack of awareness (i.e., losing track of time) by the user, and thus unintentional. Mental fatigue may result from such long intervals of IHS use. In the short term, mental fatigue by the user of an IHS may result in lower productivity. Over time, mental fatigue may result in undesirable physical and psychological consequences to users of IHSs.

SUMMARY

In various embodiments, Information Handling Systems (IHSs) may include: one or more processors; a memory device coupled to the one or more processors, the memory device storing computer-readable instructions that, upon execution by the one or more processors, cause the IHS to: upon a user of the IHS initiating a first session of operating the IHS, monitor activity in operation of the IHS by the user and monitor physiological parameters of the user; generate estimates of the user's mental fatigue during the first session based on the monitored activity by the user and the monitored physiological parameters of the user; based on the monitored activity by the user and the monitored physiological parameters of the user, identify when the user stops operating the IHS and ends the first session; based on the monitored activity by the user and the monitored physiological parameters of the user, identify when the user resumes use of the IHS and begins a second session; upon the user beginning the second session, prompt the user for their level of mental fatigue at the end of the first session; and update a machine learning model used to generate the estimates of the user's mental fatigue during the first session based on the mental fatigue level reported by the user at the end of the first session.

In some IHS embodiments, the physiological parameters of the user are monitored through use of a network interface of the IHS to communicate with at least one of sensors worn by the user of the IHS and contactless sensors in proximity to the user of the IHS. In some IHS embodiments, the sensors worn by the user of the IHS comprises of at least one of a smart watch worn by the user and a fitness tracker worn the by user. In some IHS embodiments, monitored physiological parameters of the user comprise at least one of eye movements, heart rate and breathing rate. In some IHS embodiments, the eye movements of the user are monitored using one or more optical sensors of the IHS. In some IHS embodiments, the user is identified as stopping operation of the IHS and ending the first session based a loss of connectivity with the sensors worn by the user of the IHS. In some IHS embodiments, the user is identified as stopping operation of the IHS and ending the first session based a first duration without detected activity by the user in operation of the IHS. In some IHS embodiments, the monitored activity by the user in operation of the IHS comprises at least one of keyboard inputs by the user, pointing device inputs by the user, voice command inputs by the user and software application inputs by the user. In some IHS embodiments, the machine learning model used to generate the estimates of the user's mental fatigue during the first session comprises a neural network that receives the monitored activity by the user and the monitored physiological parameters of the user as inputs and that generates the estimates of the user's mental fatigue as an output. In some IHS embodiments, the mental fatigue level reported by the user at the end of the first session is used to train the neural network to associate the activity by the user and the physiological parameters monitored during the first session with the mental fatigue level reported by the user.

In various additional embodiments, methods are provided for detecting mental fatigue by a user of an Information Handling System (IHS). The methods may include: upon a user of the IHS initiating a first session of operating the IHS, monitoring activity in operation of the IHS by the user and monitoring physiological parameters of the user; generating estimates of the user's mental fatigue during the first session based on the monitored activity by the user and the monitored physiological parameters of the user; based on the monitored activity by the user and the monitored physiological parameters of the user, identifying when the user stops operating the IHS and ends the first session; based on the monitored activity by the user and the monitored physiological parameters of the user, identifying when the user resumes use of the IHS and begins a second session; upon the user beginning the second session, prompting the user for their level of mental fatigue at the end of the first session; and updating a machine learning model used to generate the estimates of the user's mental fatigue during the first session based on the mental fatigue level reported by the user at the end of the first session.

In some method embodiments, the physiological parameters of the user are monitored through use of a network interface of the IHS to communicate with at least one of sensors worn by the user of the IHS and contactless sensors in proximity to the user of the IHS. In some method embodiments, the sensors worn by the user of the IHS comprises of at least one of a smart watch worn by the user and a fitness tracker worn the by user. In some method embodiments, the monitored physiological parameters of the user comprise at least one of eye movements, heart rate and breathing rate. In some method embodiments, the user is identified as stopping operation of the IHS and ending the first session based a loss of connectivity with the sensors worn by the user of the IHS. In some method embodiments, the machine learning model used to generate the estimates of the user's mental fatigue during the first session comprises a neural network that receives the monitored activity by the user and the monitored physiological parameters of the user as inputs and that generates the estimates of the user's mental fatigue as an output.

In various additional embodiments, computer-readable storage devices may include instructions stored thereon for detecting mental fatigue by a user of an Information Handling System (IHS), wherein execution of the instructions by one or more processors of the IHS causes the one or more processors to: upon a user of the IHS initiating a first session of operating the IHS, monitor activity in operation of the IHS by the user and monitor physiological parameters of the user; generate estimates of the user's mental fatigue during the first session based on the monitored activity by the user and the monitored physiological parameters of the user; based on the monitored activity by the user and the monitored physiological parameters of the user, identify when the user stops operating the IHS and ends the first session; based on the monitored activity by the user and the monitored physiological parameters of the user, identify when the user resumes use of the IHS and begins a second session; upon the user beginning the second session, prompt the user for their level of mental fatigue at the end of the first session; and update a machine learning model used to generate the estimates of the user's mental fatigue during the first session based on the mental fatigue level reported by the user at the end of the first session.

In some storage device embodiments, the machine learning model used to generate the estimates of the user's mental fatigue during the first session comprises a neural network that receives the monitored activity by the user and the monitored physiological parameters of the user as inputs and that generates the estimates of the user's mental fatigue as an output. In some storage device embodiments, the mental fatigue level reported by the user at the end of the first session is used to train the neural network to associate the activity by the user and the physiological parameters monitored during the first session with the mental fatigue level reported by the user. In some storage device embodiments, the user is identified as stopping operation of the IHS and ending the first session based a first duration without detected activity by the user in operation of the IHS.

BRIEF DESCRIPTION OF THE DRAWINGS

The present invention(s) is/are illustrated by way of example and is/are not limited by the accompanying figures, in which like references indicate similar elements. Elements in the figures are illustrated for simplicity and clarity, and have not necessarily been drawn to scale.

DETAILED DESCRIPTION

For purposes of this disclosure, an IHS may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, an IHS may be a personal computer (e.g., desktop or laptop), tablet computer, mobile device (e.g., Personal Digital Assistant (PDA) or smart phone), server (e.g., blade server or rack server), a network storage device, or any other suitable device and may vary in size, shape, performance, functionality, and price. An IHS may include Random Access Memory (RAM), one or more processing resources, such as a Central Processing Unit (CPU) or hardware or software control logic, Read-Only Memory (ROM), and/or other types of nonvolatile memory.

Figure 1:
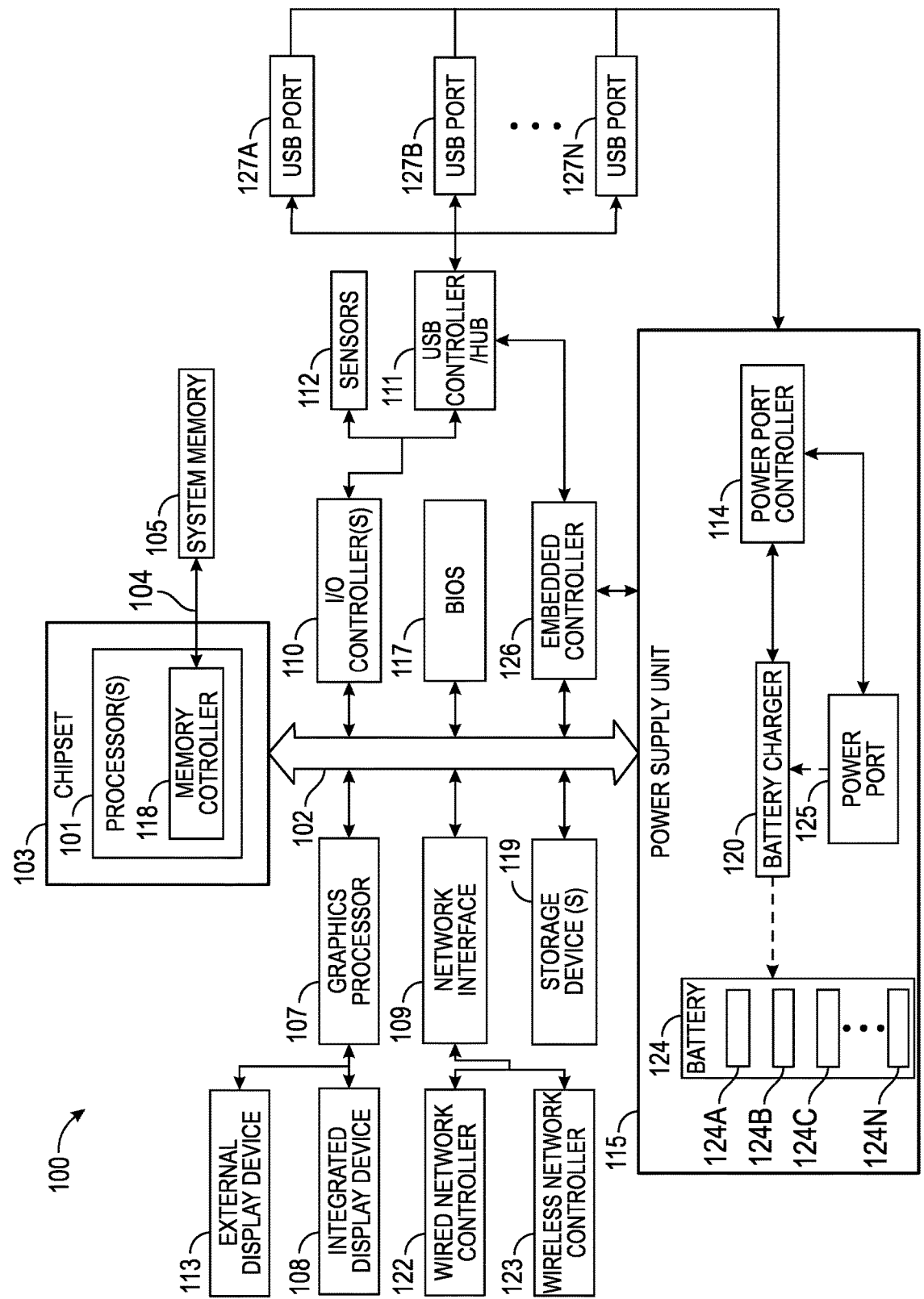
FIG. 1 is a block diagram depicting certain components of an IHS operable according to various embodiments for detecting mental fatigue by a user of the IHS.

Additional components of an IHS may include one or more disk drives, one or more network ports for communicating with external devices as well as various I/O devices, such as a keyboard, a mouse, touchscreen, and/or a video display. An IHS may also include one or more buses operable to transmit communications between the various hardware components. An example of an IHS is described in more detail below. FIG. 1 shows an example of an IHS configured to implement the systems and methods described herein according to certain embodiments. It should be appreciated that although certain IHS embodiments described herein may be discussed in the context of a personal computing device, other embodiments may be utilized.

FIG. 1 is a block diagram depicting certain components of an IHS 100 operable according to various embodiments for detecting mental fatigue by a user of the IHS. As described in additional detail below, IHS 100 may include capabilities for determining when a user of IHS 100 is actively using the IHS and when the user is taking a break from using the IHS 100, where such determinations may be made based on data collected from various I/O capabilities supported by the IHS 100. In addition, embodiments may also utilize data collected by the IHS 100 to estimate levels of mental fatigue by the user of the IHS. In response to the user taking a break from operation of the IHS 100 and then resuming operation of the IHS 100, embodiments may collect feedback from the user of the IHS 100 regarding their perceived level of mental fatigue prior to the break. In this manner, mental fatigue estimates based on data collected by the IHS 100 may be correlated to the user's reported mental fatigue, this improving machine learning models that are used to estimate the user's mental fatigue. In various embodiments, IHS 100 may include an embedded controller 126 that includes logic that executes program instructions, in conjunction with operations by components of power supply unit 115 and the operating system of IHS 100, to perform the operations disclosed herein for detecting breaks by the user of the IHS 100 and for collecting data used to identify mental fatigue by the user of the IHS. While a single IHS 100 is illustrated in FIG. 1, IHS 100 may be a component of an enterprise system that may include any number of additional IHSs that may also be configured in the same or similar manner to IHS 100.

IHS 100 includes one or more processors 101, such as a Central Processing Unit (CPU), that execute code retrieved from a system memory 105. Although IHS 100 is illustrated with a single processor 101, other embodiments may include two or more processors, that may each be configured identically, or to provide specialized processing functions. Processor 101 may include any processor capable of executing program instructions, such as an Intel Pentium™ series processor or any general-purpose or embedded processors implementing any of a variety of Instruction Set Architectures (ISAs), such as the x86, POWERPC®, ARM®, SPARC®, or MIPS® ISAs, or any other suitable ISA.

In the embodiment of FIG. 1, the processor 101 includes an integrated memory controller 118 that may be implemented directly within the circuitry of the processor 101, or the memory controller 118 may be a separate integrated circuit that is located on the same die as the processor 101. The memory controller 118 may be configured to manage the transfer of data to and from the system memory 105 of the IHS 100 via a high-speed memory interface 104. The system memory 105 that is coupled to processor 101 provides the processor 101 with a high-speed memory that may be used in the execution of computer program instructions by the processor 101. Accordingly, system memory 105 may include memory components, such as such as static RAM (SRAM), dynamic RAM (DRAM), NAND Flash memory, suitable for supporting high-speed memory operations by the processor 101. In certain embodiments, system memory 105 may combine both persistent, non-volatile memory and volatile memory. In certain embodiments, the system memory 105 may be comprised of multiple removable memory modules.

IHS 100 utilizes a chipset 103 that may include one or more integrated circuits that are connected to processor 101. In the embodiment of FIG. 1, processor 101 is depicted as a component of chipset 103. In other embodiments, all of chipset 103, or portions of chipset 103 may be implemented directly within the integrated circuitry of the processor 101. Chipset 103 provides the processor(s) 101 with access to a variety of resources accessible via bus 102. In IHS 100, bus 102 is illustrated as a single element. Various embodiments may utilize any number of buses to provide the illustrated pathways served by bus 102.

As illustrated, a variety of resources may be coupled to the processor(s) 101 of the IHS 100 through the chipset 103. For instance, chipset 103 may be coupled to a network interface 109 that may support different types of network connectivity. In certain embodiments, IHS 100 may include one or more Network Interface Controllers (NICs), each of which may implement the hardware required for communicating via a specific networking technology, such as Wi-Fi, BLUETOOTH, Ethernet and mobile cellular networks (e.g., CDMA, TDMA, LTE). As illustrated, network interface 109 may support network connections by wired network controllers 122 and wireless network controller 123. Each network controller 122, 123 may be coupled via various buses to the chipset 103 of IHS 100 in supporting different types of network connectivity, such as the network connectivity utilized by applications of the operating system of IHS 100.

Chipset 103 may also provide access to one or more display device(s) 108, 113 via graphics processor 107. In certain embodiments, graphics processor 107 may be comprised within a video or graphics card or within an embedded controller installed within IHS 100. In certain embodiments, graphics processor 107 may be integrated within processor 101, such as a component of a system-on-chip. Graphics processor 107 may generate display information and provide the generated information to one or more display device(s) 108, 113 coupled to the IHS 100. The one or more display devices 108, 113 coupled to IHS 100 may utilize LCD, LED, OLED, or other display technologies. Each display device 108, 113 may be capable of receiving touch inputs such as via a touch controller that may be an embedded component of the display device 108, 113 or graphics processor 107, or may be a separate component of IHS 100 accessed via bus 102. As illustrated, IHS 100 may support an integrated display device 108, such as a display integrated into a laptop, tablet, 2-in-1 convertible device, or mobile device. In some embodiments, IHS 100 may be a hybrid laptop computer that includes dual integrated displays incorporated in both of the laptop panels. IHS 100 may also support use of one or more external displays 113, such as external monitors that may be coupled to IHS 100 via various types of couplings. In embodiments where display devices 108 and/or 113 are touchscreen displays, inputs by the user to the touchscreen may be monitored for use in determining when the user is actively operating the IHS 100 and when the user is taking a break from using the IHS. In addition, inputs detected by touchscreen displays may be used to measure a user's level of responsiveness, such as based on the time required to respond to a prompt or the number of attempts required to perform a user interface task, for use in identifying mental fatigue by the user of the IHS 100.

In certain embodiments, chipset 103 may utilize one or more I/O controllers 110 that may each support hardware components such as user I/O devices and sensors 112. For instance, I/O controller 110 may provide access to one or more user I/O devices such as a keyboard, mouse, touchpad, touchscreen, microphone, speakers, camera and other input and output devices that may be coupled to IHS 100. Each of the supported user I/O devices may interface with the I/O controller 110 through wired or wireless connections. In some embodiments, inputs by the user to I/O devices, such as keyboards, pointing devices and microphones, that may be coupled to the IHS 100 via these I/O controllers 110 may be monitored for use in determining when the user is actively operating the IHS 100 and when the user is taking a break from using the IHS. In addition, inputs by the user to these I/O devices may be used to estimate a user's level of mental fatigue, such as based on the rate of keystroke entry, the number of erroneous keyboard entries (e.g., based on the number of deletion and backspace key entries), the number of attempts required to complete a user interface operation, the rate of speech by the user in issuing voice commands and other characteristics of the user's speech.

In certain embodiments, sensors 112 that may be accessed via I/O controllers 110 may provide access to data describing environmental and operating conditions of IHS 100. For instance, sensors 112 may include geo-location sensors capable for providing a geographic location for IHS 100, such as a GPS sensor or other location sensors configured to determine the location of IHS 100 based on triangulation and network information. Various additional sensors, such as optical, infrared and sonar sensors, that may provide support for xR (virtual, augmented, mixed reality) sessions hosted by the IHS 100. Such sensors 112 may capabilities for detecting when a user is detected within a certain proximity to IHS 100. For instance, sensors 112 may detect when a user is in close proximity to the IHS 100 and, in some cases, whether the user is facing the display(s) 108, 113. Sensors 112 may also detect when a user is not in close proximity to the IHS 100, but is nonetheless sufficiently nearby that the user may still be actively using IHS 100, such as by monitoring the progress of an application running on an IHS from across the room. In some embodiments, user proximity determinations based on information collected by sensors 112 may be monitored for use in determining when the user is actively operating the IHS 100 and when the user is taking a break from using the IHS.

In addition, data collected by sensors 112 may be used in identifying mental fatigue by the user of the IHS 100. In some embodiments, sensors 112 may collect physiological data from the user of the IHS 100. In some instances, sensors 112 may thus be wearable sensors that may provide physiological data, such as heart rate, blood pressure, and breathing rate, of the user of the IHS 100. For example, wearable sensors may include sensor capabilities supported by a smartwatch or a wearable fitness tracker. In some instances, sensors 112 may include contactless sensors that are in proximity to the user, such as an infrared sensor of the IHS that can provide estimates of the user's temperature. In some instances, contactless sensors may include radar sensors of the IHS that may be used to estimate a user's level of mental fatigue based on the speed and frequency of the user's movements. In some instances, such data may be collected from sensors 112 via wireless communications supported by the IHS 100, such as the Bluetooth interface described below. In some embodiments, sensors 112 used to identify mental fatigue may include the use of optical, infrared and sonar sensors of the IHS in order to estimate mental fatigue by the user of the IHS and to track certain movements by the user, including tracking of eye movements by the user and collecting pupil dilation information.

As illustrated, I/O controllers 110 may include a USB controller 111 that, in some embodiments, may also implement functions of a USB hub. In some embodiments, USB controller 111 may be a dedicated microcontroller that is coupled to the motherboard of IHS 100. In other embodiments, USB controller 111 may be implemented as a function of another component, such as a component of a SoC (System on Chip) of IHS 100, embedded controller 126, processors 101 or of an operating system of IHS 100. USB controller 111 supports communications between IHS 100 and one or more USB devices coupled to IHS 100, whether the USB devices may be coupled to IHS 100 via wired or wireless connections. In some embodiments, a USB controller 111 may operate one or more USB drivers that detect the coupling of USB devices and/or power inputs to USB ports 127*a-n*. USB controller 111 may include drivers that implement functions for supporting communications between IHS 100 and coupled USB devices, where the USB drivers may support communications according to various USB protocols (e.g., USB 2.0, USB 3.0). In providing functions of a hub, USB controller 111 may support concurrent couplings by multiple USB devices via one or more USB ports 127*a-n* supported by IHS 100.

Chipset 103 also provides processor 101 with access to one or more storage devices 119. In various embodiments, storage device 119 may be integral to the IHS 100, or may be external to the IHS 100. In certain embodiments, storage device 119 may be accessed via a storage controller that may be an integrated component of the storage device. Storage device 119 may be implemented using any memory technology allowing IHS 100 to store and retrieve data. For instance, storage device 119 may be a magnetic hard disk storage drive or a solid-state storage drive. In certain embodiments, storage device 119 may be a system of storage devices, such as a cloud drive accessible via network interface 109.

As illustrated, IHS 100 also includes a BIOS (Basic Input/Output System) 117 that may be stored in a non-volatile memory accessible by chipset 103 via bus 102. In some embodiments, BIOS 117 may be implemented using a dedicated microcontroller coupled to the motherboard of IHS 100. In some embodiments, BIOS 117 may be implemented as operations of embedded controller 126. Upon powering or restarting IHS 100, processor(s) 101 may utilize BIOS 117 instructions to initialize and test hardware components coupled to the IHS 100. The BIOS 117 instructions may also load an operating system for use by the IHS 100. The BIOS 117 provides an abstraction layer that allows the operating system to interface with the hardware components of the IHS 100. The Unified Extensible Firmware Interface (UEFI) was designed as a successor to BIOS. As a result, many modern IHSs utilize UEFI in addition to or instead of a BIOS. As used herein, BIOS is intended to also encompass UEFI.

Some IHS 100 embodiments may utilize an embedded controller 126 that may be a motherboard component of IHS 100 and may include one or more logic units. In certain embodiments, embedded controller 126 may operate from a separate power plane from the main processors 101, and thus from the operating system functions of IHS 100. In some embodiments, firmware instructions utilized by embedded controller 126 may be used to operate a secure execution environment that may include operations for providing various core functions of IHS 100, such as power management and management of certain operating modes of IHS 100.

Embedded controller 126 may also implement operations for interfacing with a power supply unit 115 in managing power for IHS 100. In certain instances, the operations of embedded controller may determine the power status of IHS 100, such as whether IHS 100 is operating strictly from battery power, whether any charging inputs are being received by power supply unit 115, and/or the appropriate mode for charging the one or more battery cells 124*a-n* using the available charging inputs. Embedded controller 126 may support routing and use of power inputs received via a USB port 127*a-n* and/or via a power port 125 supported by the power supply unit 115. In addition, operations of embedded controller 126 may interoperate with power supply unit 115 in order to provide battery status information, such as the charge level of the cells 124*a-n* of battery 124. In some embodiments, power status information collected by embedded controller 126 may be utilized in determining whether to operate user activity monitoring procedures, where the monitoring of user activity is used to determine when the user is actively operating the IHS 100 and when the user has taken a break from operating the IHS.

In some embodiments, embedded controller 126 may also interface with power supply unit 115 in monitoring the battery state of battery 124, such as the relative state of charge of battery 124, where this charge level of the battery 124 may be specified as a percentage of the full charge capacity of the battery 124. In some instance, when operating from power stored in battery system 124, embedded controller 126 may detect when the voltage of the battery system 124 drops below a low-voltage threshold. When the charge level of battery 124 drops below such a low-voltage threshold, embedded controller 126 may transition the IHS to an off-power state in implementing a battery protection mode that preserves a minimal power level in battery 124.

Embedded controller 126 may also implement operations for detecting certain changes to the physical configuration of IHS 100 and managing the modes corresponding to different physical configurations of IHS 100. For instance, where IHS 100 is a laptop computer or a convertible laptop computer, embedded controller 126 may receive inputs from a lid position sensor that may detect whether the two sides of the laptop have been latched together, such that the IHS is in a closed position. In response to lid position sensor detecting latching of the lid of IHS 100, embedded controller 126 may initiate operations for shutting down IHS 100 or placing IHS 100 in a low-power mode. In this manner, IHS 100 may support the use of various power modes. In some embodiments, the power modes of IHS 100 may be implemented through operations of the embedded controller 126 and power supply unit 115.

As described, IHS 100 may also include a power supply unit 115 that receives power inputs used for charging batteries 124 from which the IHS 100 operates. IHS 100 may include a power port 125 to which an AC adapter may be coupled to provide IHS 100 with a supply of DC power. The DC power input received at power port 125 may be utilized by a battery charger 120 for recharging one or more internal batteries 124 of IHS 100. As illustrated, batteries 124 utilized by IHS 100 may include one or more cells 124*a*-*n* that may connected in series or in parallel. Power supply unit 115 may support various modes for charging the cells 124*a*-*n* of battery 124 based on the power supply available to IHS 100 and based on the charge levels of the battery system 124. In certain embodiments, power supply unit 115 of IHS 100 may include a power port controller 114 that is operable for configuring operations by power port 125.

In various embodiments, an IHS 100 does not include each of the components shown in FIG. 1. In various embodiments, an IHS 100 may include various additional components in addition to those that are shown in FIG. 1. Furthermore, some components that are represented as separate components in FIG. 1 may in certain embodiments instead be integrated with other components. For example, in certain embodiments, all or a portion of the functionality provided by the illustrated components may instead be provided by components integrated into the one or more processor(s) 101 as a systems-on-a-chip.

Figure 2:
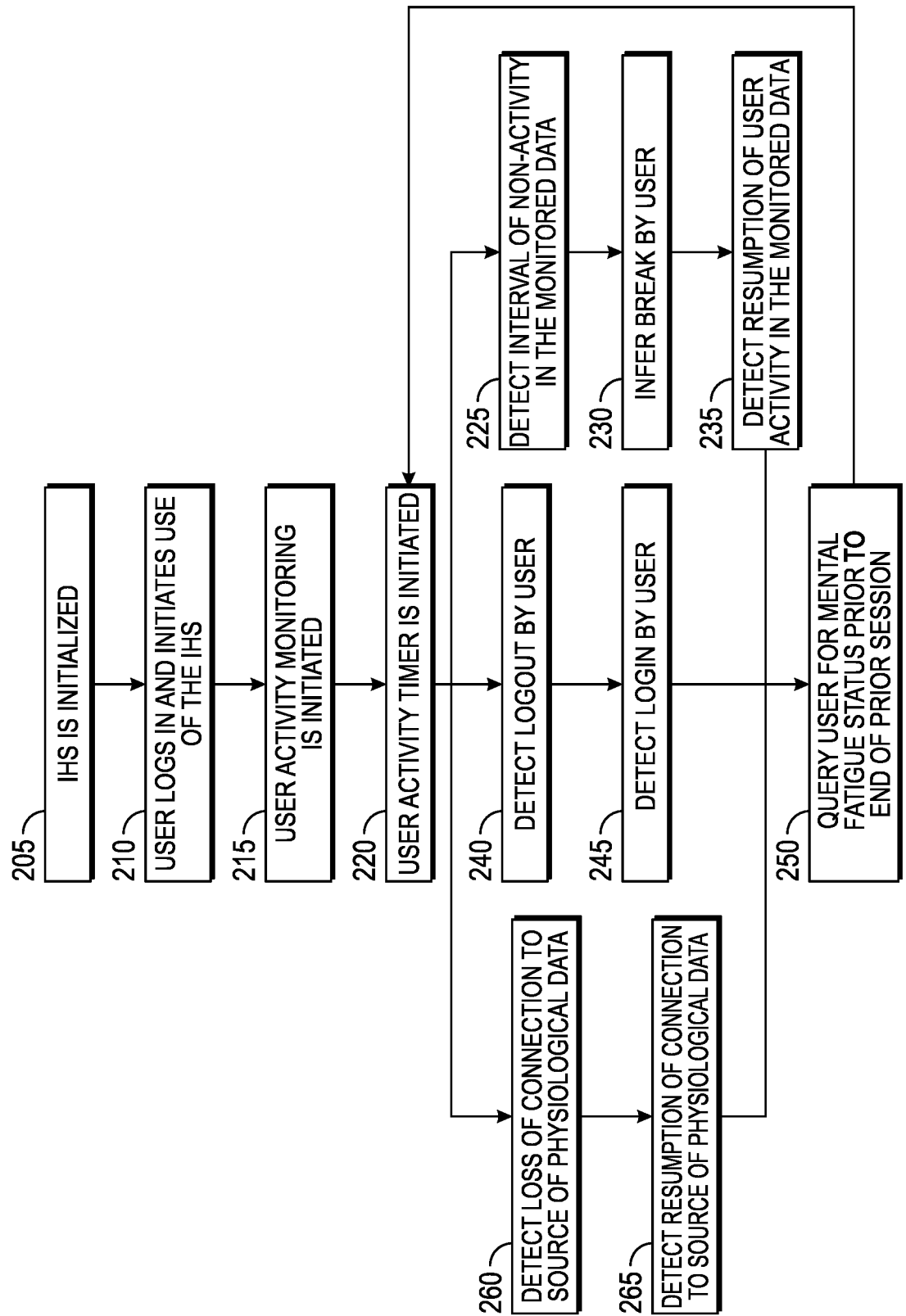
FIG. 2 is a flow chart diagram illustrating certain steps of a process according to various embodiments for detecting mental fatigue by a user of an IHS.

FIG. 2 is a flow chart diagram illustrating certain steps of a process according to various embodiments for detecting mental fatigue by a user of an IHS. As illustrated, embodiments may begin at block 205 with the initialization of an IHS, such as the IHS described with regard to FIG. 1. Once the IHS has been initialized and the operating system of the IHS is booted, at 210, the user may login to the IHS and/or operating system and may commence operation of the IHS through use of software applications that are supported by the operating system of the IHS.

Upon operation of the IHS being initiated, at 215, one or more user activity monitors may be initiated. As described with regard to FIG. 1, an IHS 100 according to embodiments may be instrumented with capabilities for monitoring activity by the user of the IHS. As described above, embodiments may also collect physiological data from the user of the IHS, where this physiological data and the user activity data may be used in generating estimates of the user's level of mental fatigue as they operate the IHS. Below, the description of FIG. 3 sets forth capabilities by which a mental fatigue models may be improved based on feedback provided by the user.

In monitoring of user activity, I/O controllers of the IHS may be configured to monitor keyboard inputs by the user. Embodiments may monitor for keyboard inputs and track the number and rate of key inputs by the user over time without collecting or recording the specific keys that are pressed by the user, thus detecting when a user is actively engaged in key entry and collecting data for use in estimating the level of mental fatigue being experienced by the user, but without capturing specific keystroke information that could potentially result in a security breach or otherwise violate the user's privacy. In a similar manner, I/O controllers of the IHS may be configured to monitor for pointing device inputs by the user, such as mouse and touchscreen inputs. As with the keyboard inputs, the pointing device inputs may be monitored without capturing the specific pointing device selections made by the user. In some embodiments, an audio controller of the IHS may be configured to monitor for speech inputs by the user, without capturing any of the specific speech inputs by the user. Even though the monitoring application does not track the specific speech inputs by the user, the user activity monitoring may nonetheless interface with speech processing capabilities of the IHS in order to discern actual user speech inputs that are recognized by the IHS from other speech by the user. In addition, speech processing capabilities may be used to evaluate characteristics of the user's speech, such as the rate of speech, speaking volume, the length of pauses and speech clarity, for use in estimating the user's level of mental fatigue.

In some embodiments, user activity monitoring may include monitoring operation of software applications of the IHS by the user. In such embodiments, the operating system of the IHS may include a user activity monitor that monitors the operation of applications by the user. In some embodiments, the monitored inputs to software applications by the user may be collected for indications of mental fatigue. For instance, inputs to software applications may provide indications of the number and rate of errors being made by the user, such as data entry errors that require corrections by the user and such as user interface errors that result in the user requiring multiple attempts to complete user interface operations.

In addition to user activity monitoring, embodiments may also initiate monitoring of physiological data pertaining to the user of the IHS. As described with regard to FIG. 1, an IHS according to embodiments may include capabilities for collecting physiological data through the use of various sensors that may be components of the IHS, or that may be components of wearable devices. In some instances, embodiments may subscribe to data streams and notifications generated by such sensors. In some instances, embodiments may periodically poll such sensors in order to collect physiological data. Based on the collected data, embodiments may generate a time series of various different physiological characteristics of the user as they operate the IHS.

With the user activity and physiological monitoring initiated, at 220, a timer is initiated for tracking the duration of the user's operation of the IHS without detecting the user taking any substantial breaks. Once the timer is initiated, as indicated in FIG. 2, at 225, embodiments detect an interval without activity in any of the monitored user activity data streams. For instance, embodiments may detect an interval of five minutes without detecting any I/O inputs (i.e., no keyboard, speech or pointing device inputs) and without detecting any user inputs to software applications running in the operating system of the IHS. Due to the lack of user inputs during this interval, embodiments may infer that user has taken a break from operation of the IHS.

Embodiments may configure this interval used as a threshold of non-activity based on various criteria, such as the length of time the user has been actively using the IHS over the prior twenty-four hours. For instance, a user that has logged two hours of IHS activity over the prior twenty-four hours may have a two-minute threshold of non-activity for inferring a break by the user, while a user that has logged twelve hours of IHS activity over the prior twenty-four hours may have a five-minute threshold of non-activity for inferring a break. In this manner, relatively short durations of non-activity may suffice for inferred breaks for users with less IHS activity, while users with substantial amounts of activity may require longer thresholds of non-activity before a sufficient break is inferred for that user.

Upon detecting a sufficient interval of non-activity by the user, at 230, a break by the user is inferred. Through this interval of non-activity, the activity monitoring capabilities of the IHS nonetheless continue to monitor for any activity by the user. Once activity by the user is detected, at 235, the user is deemed to have resumed active operation of the IHS. In some embodiments, the user is not deemed to have resumed active operation of the IHS until a substantial amount of activity is detected, with minimal inputs, such as a user initiating a streaming music player, not being indicative of a user resuming active operation of the IHS. As described in additional detail below, if the user's inputs are sufficient to indicate a resumption of the user's operation of the IHS, at 250, embodiments may query the user to provide feedback regarding their level of mental fatigue prior to the taking the break.

As indicated in FIG. 2, at 240, breaks by a user may be expressly indicated by the user logging out of the IHS. In such instances, a user may actively log out of the IHS, such as through capabilities provided by the operating system of the IHS. In other instances, a user may be automatically logged out by the operating system of the IHS. At 245, embodiments may detect the user has logged back in to the IHS. Also as indicated in FIG. 2, once the user has logged back in to the IHS to start a new session, at 250, embodiments may query the user to provide feedback regarding their level of mental fatigue at the time they logged out to end the prior session.

Embodiments may additionally infer a break by the user based on the status of physiological data streams that are being monitored. In such embodiments, at 260, a loss of connection with one or more sources of physiological data is detected. For instance, embodiments may collect physiological data from sensors worn by the user, such as from personal fitness tracking devices and smartwatches. In instances where the user leaves the area where the IHS is located, the IHS eventually losses connectivity with the wearable devices. Embodiments may utilize configurable thresholds for durations of connectivity losses that suffice as indicators of a break from operation of the IHS. For instance, a short loss in connectivity may be insufficient to infer the user has taken a break, such as loss in connectivity resulting from the user leaving the IHS to retrieve documents from a printer or to retrieve another item from the immediate area. Upon detecting a loss of connectivity with a physiological sensor for a duration longer than the configured threshold, at 265, a break by the user is inferred and embodiments detect a resumption in the connection to the source of physiological data. As above, at 250, once the user resumes operation of the IHS, embodiments may query the user to provide feedback regarding their level of mental fatigue at the time they left the area in which the IHS is located, thus resulting in the loss of connectivity with the physiological sensors.

Figure 3:
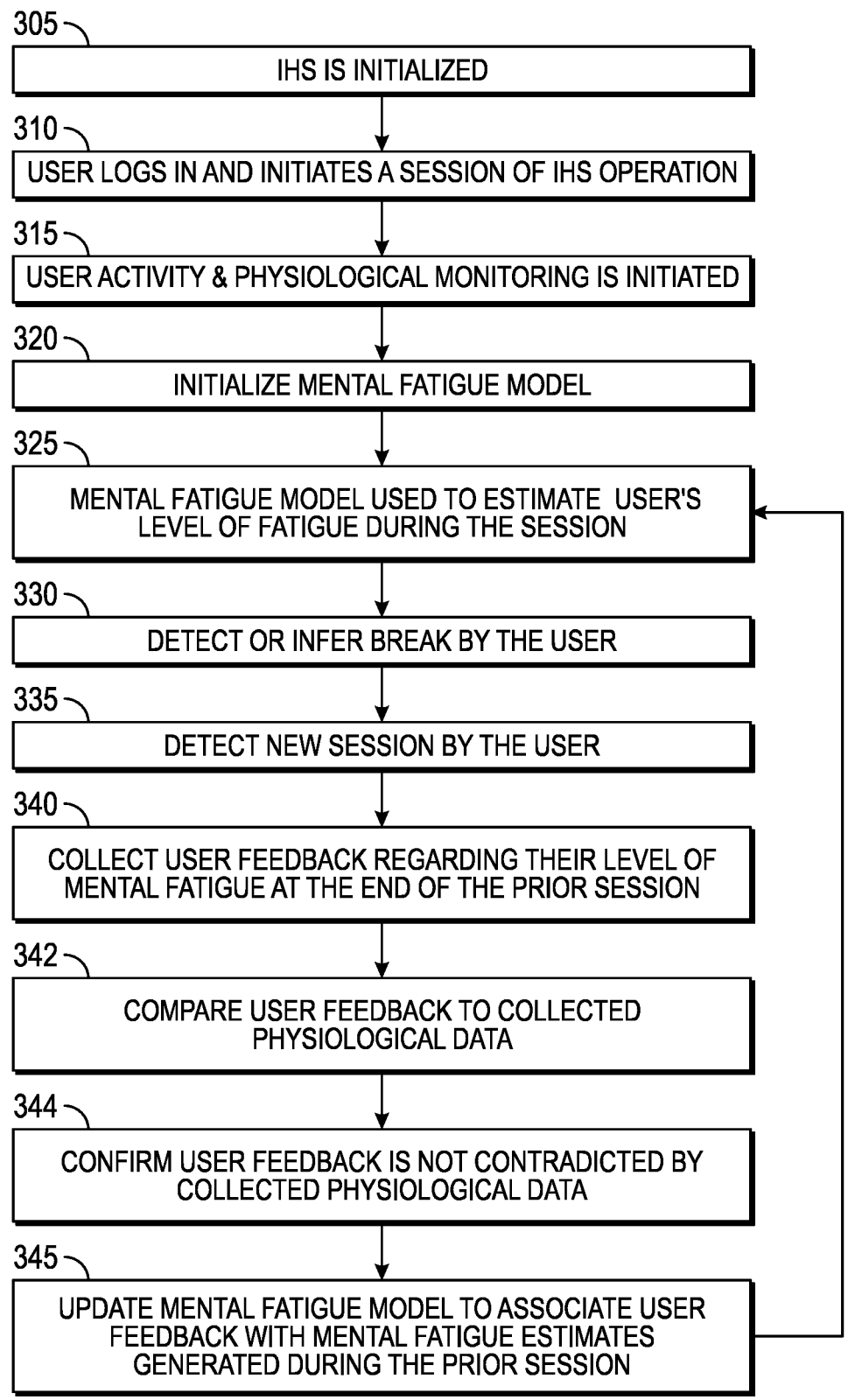
FIG. 3 is a flow chart diagram illustrating certain steps of a process according to various embodiments for detecting mental fatigue by a user of an IHS and for improving a model used to detect the mental fatigue.

FIG. 3 is a flow chart diagram illustrating certain steps of a process according to various embodiments for detecting mental fatigue by a user of an IHS and for improving a model used to detect the mental fatigue. As with the embodiment of FIG. 2, the embodiment of FIG. 3 may begin at block 305 with the initialization of an IHS, such as the IHS described with regard to FIG. 1. Once the IHS has been initialized and the operating system of the IHS is booted, at 310, the user may login to the IHS and/or operating system and may commence operation of the IHS through use of software applications that are supported by the operating system of the IHS.

As before, upon operation of the IHS being initiated, at 315, one or more user activity and physiological data monitors may be initiated. As described above, an IHS 100 according to embodiments may be instrumented with capabilities for monitoring activity by the user of the IHS, where such activity monitoring may include tracking inputs by the user to applications operating on the IHS and user inputs detected by I/O devices (e.g., keyboard, pointing device) of the IHS. Also as described, an IHS 100 may include capabilities for monitoring physiological data, such as heart rate and breathing rate data collected from wearable sensors and such as eye tracking using optical sensors of the IHS.

In addition to initiating tracking of user activity and physiological data, at 320, embodiments also initiate a model for estimating the mental fatigue of the user of the IHS. Embodiments may utilize a variety of machine learning techniques for modeling a user's mental fatigue. For instance, a mental fatigue model maybe implemented using neural networks that receive the various streams of collected user activity and physiological data as inputs and that generates an estimate of the user's level of mental fatigue based on these inputs. Some embodiments may utilize Adaptive Resonance Theory neural networks that may be incrementally trained to associate the user activity and physiological data with different levels of mental fatigue that are reported by the user of the IHS in response the query issued each time the user resumes operation of the IHS. Training a mental fatigue model using traditional supervised learning is infeasible in light of the fact that every user will express mental fatigue differently, and thus through different levels of degradation in user activity and through different physiological indicators. Accordingly, as described in additional detail below, embodiments support training of the mental fatigue model using feedback provided by the user.

Once the mental fatigue model is initialized, it is supplied with the collected user activity and physiological data. Based on this collected data, at 325, the mental fatigue model outputs periodic estimates of the user's mental fatigue status. In some embodiments, the mental fatigue model may be implemented such that it outputs a categorization of the user's mental fatigue, such as classifying the user's mental status as alert, neutral, or tired. In some embodiments, the mental fatigue model may be output a numeral categorization of the user's mental fatigue, such as a mental fatigue score that may range between 1 and 10. Mental fatigue estimates are generated by the model throughout the duration of a session in which the user is actively operating the IHS. These mental fatigue estimates generated by the model are then stored by embodiments for use in training, and thus improving, the mental fatigue model.

As described above, based on monitored user activity, explicit logouts and loss of connectivity with sensors providing physiological data, at 330, breaks by the user may be detected and/or inferred. Also as described above, during the break, embodiments may continue monitoring for a user logging back in to the IHS, a resumption in user activity, and/or a resumption connectivity with physiological data sensors. Based on this monitoring, at 335, it is determined to that the user has initiated a new session. Accordingly, immediately upon detection the user resuming operation of the IHS, at 340, embodiments present the user with a request for feedback regarding their level of mental fatigue at the end of their prior session, and thus immediately before taking a break.

Embodiments may collect mental fatigue from the user in a variety of manners. In some instances, a user may be presented with a user interface dialog prompting them to specify their level of mental fatigue when ending the prior session. The prompt may request the user to classify their level of mental fatigue at the end of the prior session according to categories such as those above, where the user selects from choices such as 'alert,' 'neutral,' 'tired' and 'very tired.' In some instances, the prompt may request the user to specify their level of mental fatigue at the end of the prior session according to a numerical scale, such as on a scale between one and ten. In some embodiments, the prompt that is presented to the user may specify the time of the user's last session and the last software application that the user operated prior to taking the break. For instance, the prompt may request the user to specify their level of mental fatigue at the end of the prior session the was ended 30 minutes prior and may further specify the name of a spreadsheet or other document that was being edited at the end of that prior session.

By waiting to collect feedback until the user has taken a break and resumed operation of the IHS, embodiments collect mental fatigue data that is more accurate than data collected from the user prior to the break, or data collected at a later time. If the user were prompted to specify their level of mental fatigue prior to ending their last session, the collected data will tend to be inaccurate and thus unreliable. In scenarios where the user is tired at the end of the prior session, the user will be unable to accurately assess their own level of fatigue, since the user is in fact tired. Other problems result if users are prompted to specify their level of mental fatigue during a session, such as requesting mental fatigue feedback from the user at periodic intervals. Some users may tend to misrepresent their level of mental fatigue in response to repeated prompts during a session due to these users perceiving that their performance will be reviewed negatively due to repeated admissions of being tired. Any such misrepresentations result in inaccurate and unreliable data being generated. In addition, requesting mental fatigue estimates repeatedly throughout a session tends to affect the estimates that are provided by the user, thus resulting in further collection of inaccurate and unreliable data. For instance, if a user provides feedback of being in a tired state at any point during the session, any additional feedback following that report will also report the user being in a tired state. As such, a user stating that they are tired tends to influence following estimates during that session. In some instances, repeated querying of the user for mental fatigue estimates carries over to following sessions as the user's repeated mental fatigue admissions become self-reinforcing. Embodiments collect user feedback only at the beginning of a new session, when the user is presumably alert, and are only prompted for a limited number of estimates. Embodiments do not request a user to provide an estimate of the mental fatigue in an ongoing session, thus avoiding the user's estimates affecting their perception of their current session.

Despite the advantages of waiting to collect user feedback of mental fatigue until after the user has returned from a break, some user's may be reluctant to admitting their actual levels of fatigue and may thus provide feedback that is not truthful, or that underreports their fatigue levels. In order to detect such scenario, at 342, embodiments may compare the user's reported levels of mental fatigue to the physiological data that was reported during the prior session. Embodiments may evaluate whether the level of mental fatigue reported by the user comports with the physiological data from the prior session. For instance, a user reporting no fatigue at the end of the prior session may be considered dubious when the user's physiological data from the prior session reveals the user had a breathing rate and pupil activity consistent with an individual that is experiencing significant lethargy. Accordingly, at 344, embodiments may confirm that the user's reported level of mental fatigue at the end of the prior session is not inconsistent with their physiological data collected from that prior session.

Upon collecting mental fatigue feedback from the user and confirming the feedback is not inconsistent with the collected physiological data, at 345, this collected information is used to update the mental fatigue model, such as by training neural networks utilized by the model. In particular, upon receiving user feedback reporting their level of mental fatigue at the end of the prior session, this user activity and/or physiological data collected during the prior session is provided as a training input to the mental fatigue model along with the user's reported level of mental fatigue at the end of that prior session. In this manner, the machine learning utilized by the mental fatigue model is trained to generate a correspondence between inputs such as the data collected during the prior session and the mental fatigue status reported by the user. The mental fatigue model is thus iteratively improved, and may thus be used to more accurately assess the level of mental fatigue by the user.

It should be understood that various operations described herein may be implemented in software executed by processing circuitry, hardware, or a combination thereof. The order in which each operation of a given method is performed may be changed, and various operations may be added, reordered, combined, omitted, modified, etc. It is intended that the invention(s) described herein embrace all such modifications and changes and, accordingly, the above description should be regarded in an illustrative rather than a restrictive sense.

The terms "tangible" and "non-transitory," as used herein, are intended to describe a computer-readable storage medium (or "memory") excluding propagating electromagnetic signals; but are not intended to otherwise limit the type of physical computer-readable storage device that is encompassed by the phrase computer-readable medium or memory. For instance, the terms "non-transitory computer readable medium" or "tangible memory" are intended to encompass types of storage devices that do not necessarily store information permanently, including, for example, RAM. Program instructions and data stored on a tangible computer-accessible storage medium in non-transitory form may afterwards be transmitted by transmission media or signals such as electrical, electromagnetic, or digital signals, which may be conveyed via a communication medium such as a network and/or a wireless link.

Although the invention(s) is/are described herein with reference to specific embodiments, various modifications and changes can be made without departing from the scope of the present invention(s), as set forth in the claims below. Accordingly, the specification and figures are to be regarded in an illustrative rather than a restrictive sense, and all such modifications are intended to be included within the scope of the present invention(s). Any benefits, advantages, or solutions to problems that are described herein with regard to specific embodiments are not intended to be construed as a critical, required, or essential feature or element of any or all the claims.

Unless stated otherwise, terms such as "first" and "second" are used to arbitrarily distinguish between the elements such terms describe. Thus, these terms are not necessarily intended to indicate temporal or other prioritization of such elements. The terms "coupled" or "operably coupled" are defined as connected, although not necessarily directly, and not necessarily mechanically. The terms "a" and "an" are defined as one or more unless stated otherwise. The terms "comprise" (and any form of comprise, such as "comprises" and "comprising"), "have" (and any form of have, such as "has" and "having"), "include" (and any form of include, such as "includes" and "including") and "contain" (and any form of contain, such as "contains" and "containing") are open-ended linking verbs. As a result, a system, device, or apparatus that "comprises," "has," "includes" or "contains" one or more elements possesses those one or more elements but is not limited to possessing only those one or more elements. Similarly, a method or process that "comprises," "has," "includes" or "contains" one or more operations possesses those one or more operations but is not limited to possessing only those one or more operations.

The invention claimed is:

1. An Information Handling System (IHS) comprising:
   one or more processors;
   a memory device coupled to the one or more processors, the memory device storing computer-readable instructions that, upon execution by the one or more processors, cause the IHS to:
      upon a user of the IHS initiating a first session of operating the IHS, monitor activity in operation of the IHS by the user and monitor physiological parameters of the user, wherein the physiological parameters of the user are monitored through collection of data by one or more sensors of the IHS and also through the collection of data by a wireless network controller of the IHS interfacing with remote sensors comprising at least one of: sensors worn by the user of the IHS and contactless sensors in proximity to the user of the IHS;
      generate estimates of the user's mental fatigue during the first session based on the monitored activity by the user and the monitored physiological parameters of the user, and further based on the data collected by the one or more sensors of the IHS and the data collected by wireless network controller from the one or more remote sensors;
      based on the monitored activity by the user and the monitored physiological parameters of the user, identify when the user stops operating the IHS and ends the first session;
      based on the monitored activity by the user and the monitored physiological parameters of the user, identify when the user resumes use of the IHS and begins a second session;
      upon the user beginning the second session, prompt the user for their level of mental fatigue at the end of the first session; and
      update a machine learning model used to generate the estimates of the user's mental fatigue during the first session based on the mental fatigue level reported by the user at the end of the first session.

2. The IHS of claim 1, wherein the physiological parameters are evaluated to infer a break by the user, indicating the end of the first session.

3. The IHS of claim 2, wherein the user is identified as stopping operation of the IHS and ending the first session based a loss of connectivity with the sensors worn by the user of the IHS.

4. The IHS of claim 2, wherein the monitored activity by the user in operation of the IHS comprises at least one of keyboard inputs by the user, pointing device inputs by the user, voice command inputs by the user and software application inputs by the user.

5. The IHS of claim 1, wherein the sensors worn by the user of the IHS comprises of at least one of a smart watch worn by the user and a fitness tracker worn the by user.

6. The IHS of claim 1, wherein the monitored physiological parameters of the user comprise at least one of eye movements, heart rate and breathing rate.

7. The IHS of claim 6, wherein the eye movements of the user are monitored using one or more optical sensors of the IHS.

8. The IHS of claim 1, wherein the user is identified as stopping operation of the IHS and ending the first session based a first duration without detected activity by the user in operation of the IHS.

9. The IHS of claim 1, wherein the machine learning model used to generate the estimates of the user's mental fatigue during the first session comprises a neural network that receives the monitored activity by the user and the monitored physiological parameters of the user as inputs and that generates the estimates of the user's mental fatigue as an output.

10. The IHS of claim 9, wherein the mental fatigue level reported by the user at the end of the first session is used to train the neural network to associate the activity by the user and the physiological parameters monitored during the first session with the mental fatigue level reported by the user.

11. A method for detecting mental fatigue by a user of an Information Handling System (IHS), the method comprising:
   upon a user of the IHS initiating a first session of operating the IHS, monitoring activity in operation of the IHS by the user and monitoring physiological parameters of the user, wherein the physiological parameters of the user are monitored through collection of data by one or more sensors of the IHS and also through the collection of data by a wireless network controller of the IHS interfacing with remote sensors comprising at least one of: sensors worn by the user of the IHS and contactless sensors in proximity to the user of the IHS;
   generating estimates of the user's mental fatigue during the first session based on the monitored activity by the user and the monitored physiological parameters of the user, and further based on the data collected by the one or more sensors of the IHS and the data collected by wireless network controller from the one or more remote sensors;
   based on the monitored activity by the user and the monitored physiological parameters of the user, identifying when the user stops operating the IHS and ends the first session;
   based on the monitored activity by the user and the monitored physiological parameters of the user, identifying when the user resumes use of the IHS and begins a second session;
   upon the user beginning the second session, prompting the user for their level of mental fatigue at the end of the first session; and updating a machine learning model used to generate the estimates of the user's mental fatigue during the first session based on the mental fatigue level reported by the user at the end of the first session.

12. The method of claim 11, wherein the physiological parameters are evaluated to infer a break by the user, indicating the end of the first session.

13. The method of claim 12, wherein the user is identified as stopping operation of the IHS and ending the first session based a loss of connectivity with the sensors worn by the user of the IHS.

14. The method of claim 11, wherein the sensors worn by the user of the IHS comprises of at least one of a smart watch worn by the user and a fitness tracker worn the by user.

15. The method of claim 11, wherein the monitored physiological parameters of the user comprise at least one of eye movements, heart rate and breathing rate.

16. The method of claim 11, wherein the machine learning model used to generate the estimates of the user's mental fatigue during the first session comprises a neural network that receives the monitored activity by the user and the monitored physiological parameters of the user as inputs and that generates the estimates of the user's mental fatigue as an output.

17. A computer-readable storage device having instructions stored thereon for detecting mental fatigue by a user of an Information Handling System (IHS), wherein execution of the instructions by one or more processors of the IHS causes the one or more processors to:

upon a user of the IHS initiating a first session of operating the IHS, monitor activity in operation of the IHS by the user and monitor physiological parameters of the user, wherein the physiological parameters of the user are monitored through collection of data by one or more sensors of the IHS and also through the collection of data by a wireless network controller of the IHS interfacing with remote sensors comprising at least one of: sensors worn by the user of the IHS and contactless sensors in proximity to the user of the IHS;

generate estimates of the user's mental fatigue during the first session based on the monitored activity by the user and the monitored physiological parameters of the user, and further based on the data collected by the one or more sensors of the IHS and the data collected by wireless network controller from the one or more remote sensors;

based on the monitored activity by the user and the monitored physiological parameters of the user, identify when the user stops operating the IHS and ends the first session;

based on the monitored activity by the user and the monitored physiological parameters of the user, identify when the user resumes use of the IHS and begins a second session;

upon the user beginning the second session, prompt the user for their level of mental fatigue at the end of the first session; and update a machine learning model used to generate the estimates of the user's mental fatigue during the first session based on the mental fatigue level reported by the user at the end of the first session.

18. The computer-readable storage device of claim 17, wherein the machine learning model used to generate the estimates of the user's mental fatigue during the first session comprises a neural network that receives the monitored activity by the user and the monitored physiological parameters of the user as inputs and that generates the estimates of the user's mental fatigue as an output.

19. The computer-readable storage device of claim 18, wherein the mental fatigue level reported by the user at the end of the first session is used to train the neural network to associate the activity by the user and the physiological parameters monitored during the first session with the mental fatigue level reported by the user.

20. The computer-readable storage device of claim 17, wherein the user is identified as stopping operation of the IHS and ending the first session based a first duration without detected activity by the user in operation of the IHS.

* * * * *